(12) United States Patent
Laine

(10) Patent No.: US 9,888,993 B2
(45) Date of Patent: Feb. 13, 2018

(54) EMBOLIC PROTECTION DEVICE

(71) Applicant: St. Jude Medical, Cardiology Division, Inc., St. Paul, MN (US)

(72) Inventor: Robert M. Laine, Plymouth, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 281 days.

(21) Appl. No.: 13/782,657

(22) Filed: Mar. 1, 2013

(65) Prior Publication Data
US 2014/0249565 A1    Sep. 4, 2014

(51) Int. Cl.
*A61F 2/01*    (2006.01)

(52) U.S. Cl.
CPC ........ *A61F 2/013* (2013.01); *A61F 2002/016* (2013.01); *A61F 2230/008* (2013.01); *A61F 2230/0067* (2013.01); *A61F 2250/0063* (2013.01)

(58) Field of Classification Search
CPC ................ A61F 2/013; A61F 2002/016; A61F 2250/0063; A61F 2230/008; A61F 2230/0067
See application file for complete search history.

(56) References Cited

U.S. PATENT DOCUMENTS

| | | |
|---|---|---|
| 5,279,573 A | 1/1994 | Klosterman |
| 5,800,457 A * | 9/1998 | Gelbfish .................. A61F 2/01 606/200 |
| 5,800,525 A | 9/1998 | Bachinski et al. |
| 5,906,641 A | 5/1999 | Thompson et al. |
| 6,361,545 B1 | 3/2002 | Macoviak et al. |

(Continued)

FOREIGN PATENT DOCUMENTS

| | | |
|---|---|---|
| WO | 0053119 A1 | 9/2000 |
| WO | 2006131930 A2 | 12/2006 |

(Continued)

OTHER PUBLICATIONS

U.S. Appl. No. 13/782,703, filed Mar. 1, 2013.

(Continued)

*Primary Examiner* — Katherine M Shi
*Assistant Examiner* — Michael Mendoza
(74) *Attorney, Agent, or Firm* — Lerner, David, Littenberg, Krumholz & Mentlik, LLP

(57) ABSTRACT

Embolic protection devices useful for filtering emboli during interventional cardiac, vascular, or other procedures are described. The device can include first and second expandable mesh filters having open and closed ends. The first filter is attached to a catheter at its closed end. The second filter is attached to a steerable guide wire at its closed end. The second filter includes a cinching wire circumferentially attached to the filter. The filters are deployed in separate vessels, such as the brachiocephalic artery and the left common carotid artery. A procedure is performed, and the filters trap any emboli travelling through the path of the filters. At the end of the procedure, the second filter is closed using the cinching wire, and retracted into the first filter. Both the first and second filters are collapsed into a sheath and removed from the body with along with any emboli trapped in the filters.

19 Claims, 7 Drawing Sheets

(56) References Cited

U.S. PATENT DOCUMENTS

| | | | |
|---|---|---|---|
| 6,540,767 B1* | 4/2003 | Walak | A61F 2/01 606/200 |
| 2001/0044634 A1* | 11/2001 | Don Michael et al. | 606/200 |
| 2003/0004539 A1* | 1/2003 | Linder | A61F 2/013 606/200 |
| 2004/0215167 A1 | 10/2004 | Belson | |
| 2006/0100662 A1* | 5/2006 | Daniel | A61B 17/221 606/200 |
| 2006/0161241 A1 | 7/2006 | Barbut et al. | |
| 2006/0229658 A1 | 10/2006 | Stivland | |
| 2006/0293706 A1 | 12/2006 | Shimon | |
| 2009/0187210 A1 | 7/2009 | Mackiewicz | |
| 2009/0254172 A1 | 10/2009 | Grewe | |
| 2009/0326575 A1 | 12/2009 | Galdonik et al. | |
| 2010/0312268 A1 | 12/2010 | Belson | |
| 2011/0190863 A1 | 8/2011 | Ostroot et al. | |
| 2011/0282379 A1 | 11/2011 | Lee et al. | |
| 2012/0172920 A1 | 7/2012 | Fifer et al. | |
| 2013/0046330 A1 | 2/2013 | McIntosh et al. | |
| 2014/0172006 A1 | 6/2014 | Stack et al. | |
| 2014/0180329 A1 | 6/2014 | Krahbichler | |

FOREIGN PATENT DOCUMENTS

| | | |
|---|---|---|
| WO | 2008066881 A1 | 6/2008 |
| WO | 2008073964 A2 | 6/2008 |
| WO | 2013074521 A1 | 5/2013 |
| WO | 2013134194 A1 | 9/2013 |

OTHER PUBLICATIONS

U.S. Appl. No. 13/782,755, filed Mar. 1, 2013.
U.S. Appl. No. 13/782,677, filed Mar. 1, 2013.
International Search Report for Application No. PCT/US2013/078301 dated Mar. 28, 2014.

* cited by examiner

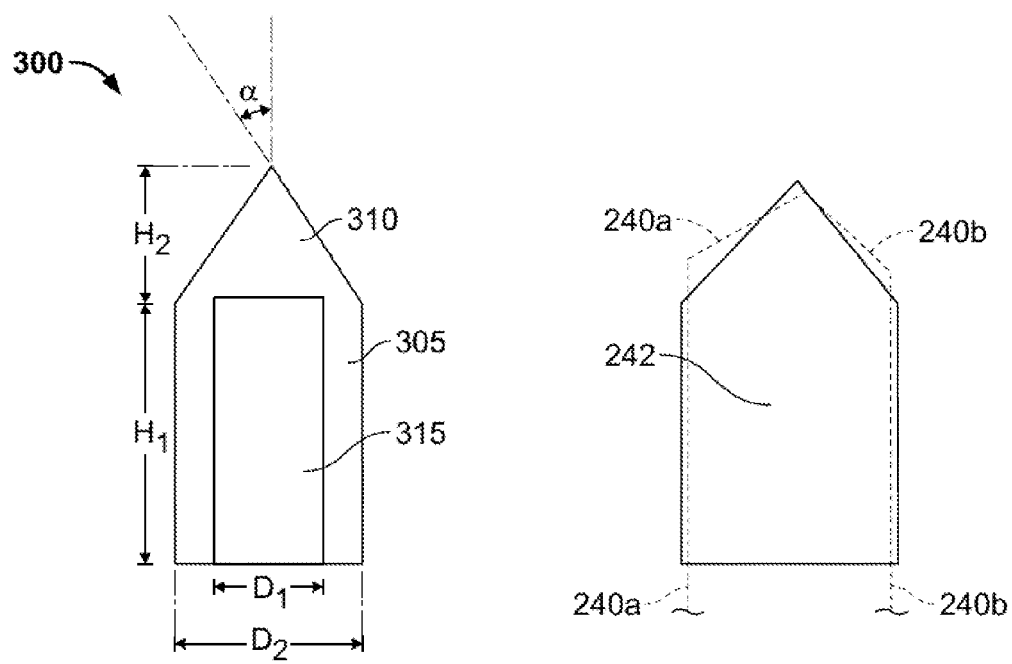
FIG. 8
FIG. 9
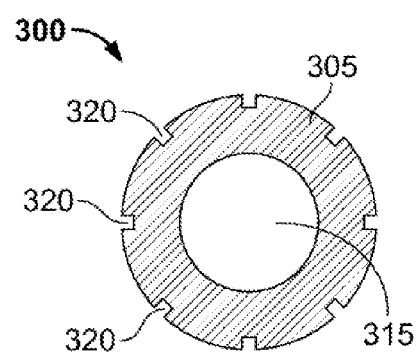
FIG. 10

EMBOLIC PROTECTION DEVICE

BACKGROUND OF THE DISCLOSURE

The present disclosure is related to protecting against embolism, and more particularly to devices, systems, and methods for the filtration and removal of debris within blood vessels.

Arterial embolism is a sudden interruption of blood flow to an organ or body part due to an embolus, e.g., debris or a clot. During a surgical intervention, such as a cardiac intervention, a vascular intervention, or a coronary intervention, tissue, plaque, and/or other masses may be dislodged due to the intervention, resulting in an embolus. These emboli are capable of traveling far from their origins, migrating to other sites of the vasculature and resulting in potentially life threatening complications. For example, an embolus may travel through the carotid artery and inhibit the flow of blood to the brain, which may result in the death of brain cells, i.e., cause a stroke. A blockage of the carotid arteries is the most common cause of a stroke.

BRIEF SUMMARY OF THE DISCLOSURE

In one embodiment according to the present disclosure, an embolic protection device includes a first filter having an open end and a closed end, the closed end being connected to a tube having a conduit. The device also includes a second filter having an open end and a closed end. The second filter is connected to a first wire, and the first wire extends into the conduit of the tube. A second wire has a first portion and a second portion. The first portion of the second wire is circumferentially attached to the open end of the second filter, and the second portion of the second wire extends into the conduit of the tube.

In another embodiment according to the present disclosure, a method of providing embolic protection to a patient includes the steps of delivering a sheath into a first blood vessel of the patient, the sheath housing a first filter and a second filter, deploying the first filter in the first blood vessel with a first guide structure, and deploying the second filter in a second blood vessel with a second guide structure. An additional step includes cinching an open end of the second filter with a cinching wire attached to the open end of the second filter.

In another embodiment according to the present disclosure, an embolic protection device includes a first filter having a closed proximal end and an open distal end, the closed proximal end having a conical shape and the open distal end having a cylindrical shape. The device also includes a second filter having an open proximal end and a closed distal end, the open proximal end having a cylindrical shape and the closed distal end having a conical shape. The device additionally includes a catheter having a proximal end, a distal end, and a lumen extending therebetween, the distal end of the catheter being fixed to the closed proximal end of the first filter. The device includes a steerable guide wire having a proximal end and a distal end, the distal end of the steerable guide wire being fixed to the closed distal end of the second filter. The device further includes a cinching wire having a first portion and a second portion, the first portion of the cinching wire being circumferentially attached to the open proximal end of the second filter. The steerable guide wire and the second portion of the cinching wire extend through the open distal end of the first filter and further through the lumen of the catheter.

In still a further embodiment according to the present disclosure, an embolic protection device includes a first filter and a second filter, each filter having an open end and a closed end defining an interior region therebetween. The device includes a catheter coupled to the closed end of the first filter. A first wire extends through a portion of the catheter and the interior regions of the first and second filters, and has an end attached to the closed end of the second filter. The second filter is configured to be at least partially received within the interior region of the first filter by manipulation of the first wire.

BRIEF DESCRIPTION OF THE DRAWINGS

FIG. 8 illustrates a vertical sectional view of an inner mold used to produce a filter for an embolic protection device according to an embodiment of the present disclosure.

FIG. 9 illustrates a schematic view of the positioning of struts in a filter of an embolic protection device according to an embodiment of the present disclosure.

FIG. 10 illustrates a horizontal sectional view of an alternate embodiment of an inner mold used to produce a filter for an embolic protection device according to an embodiment of the present disclosure.

DETAILED DESCRIPTION

Figure 1:
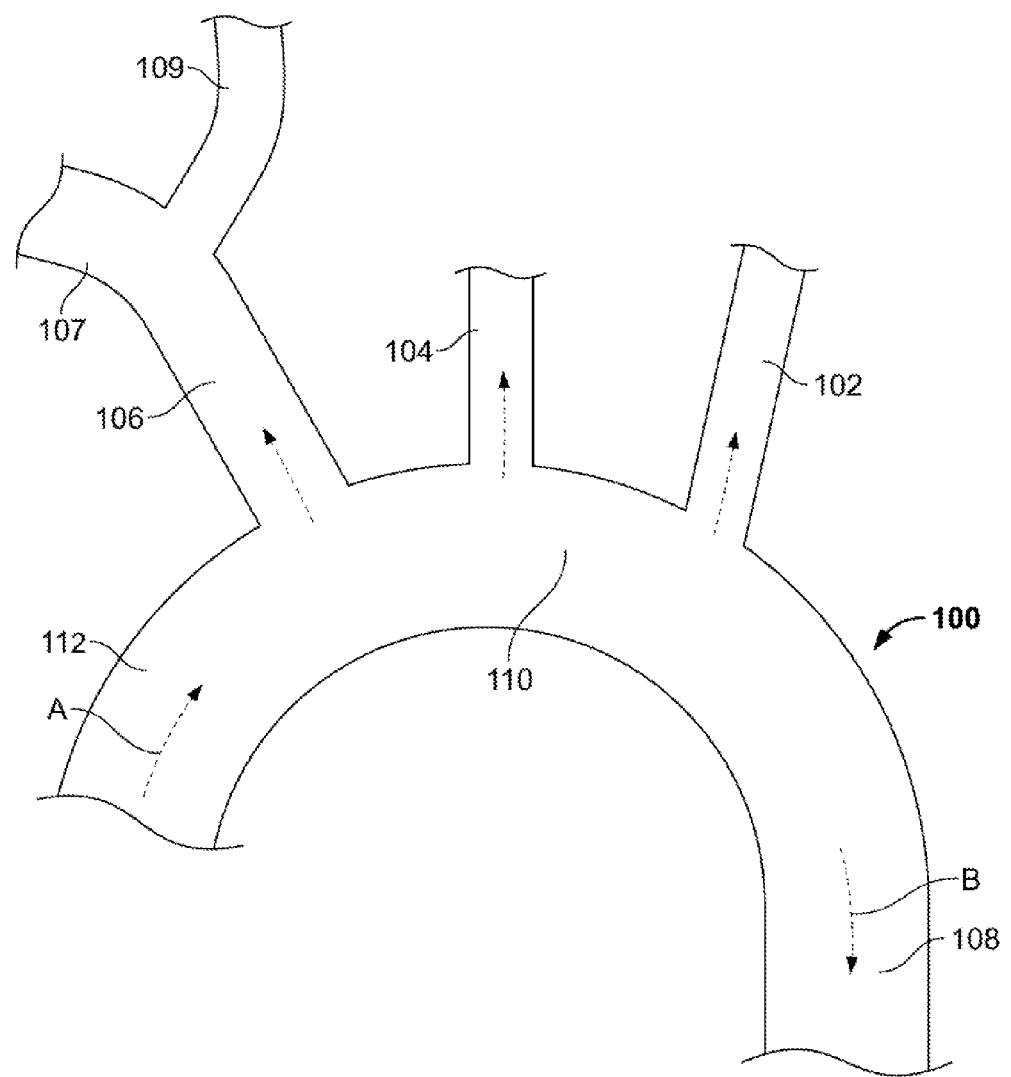
FIG. 1 illustrates a schematic view of the aorta.

A continuing need exists for devices and systems that inhibit emboli from traveling to parts of a patient's vasculature where they may block blood flow to critical organs and threaten the life of the patient.

Particular embodiments of the present disclosure are described with reference to the accompanying drawings. In the figures and in the description that follow, like reference numerals identify similar or identical elements. As shown in the drawings and as described throughout the following description, the term "proximal" refers to the end of the device that is closer to the user and the term "distal" refers to the end of the device that is farther from the user.

FIG. 1 illustrates aorta 100, the largest artery in the body, originating from the left ventricle (not shown) and extending down to the abdomen. Blood flows as indicated by arrow "A" from the left ventricle, through the aortic valve (not shown), through ascending aorta 112 to aortic arch 110. Three major arteries branch from aortic arch 110. Brachiocephalic artery 106 branches into right subclavian artery 107, supplying blood to the right arm, and right common carotid artery 109, supplying blood to the head and neck. Left common carotid artery 104 supplies blood to the head and neck. Left subclavian artery 102 supplies blood to the left arm. Blood from ascending aorta 112 not passing through one of these three arteries continues down descending aorta 108 as shown by arrow "B". Variations of the anatomy illustrated in FIG. 1 are possible and sometimes are relatively common. For example, about 10% of the population has a common brachiocephalic trunk, in which both common carotid arteries 104, 109 and right subclavian artery 107 arise from a single trunk off aortic arch 110. During interventional surgical, cardiac, and/or vascular procedures, there is a risk that emboli may break free and travel up ascending artery 112 and cause a blockage of brachiocephalic artery 106, right common carotid artery 109, and/or left common carotid artery 104, causing reduced blood flow to the brain and possibly a stroke. Devices and methods described herein may be used during interventional procedures to capture and remove emboli from the body.

Figure 2:
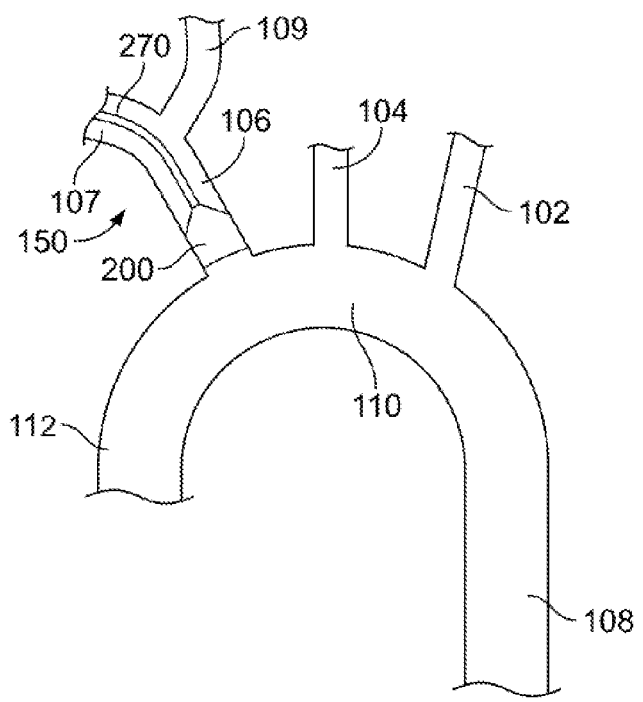
FIG. 2 illustrates a schematic view of a proximal basket of an embolic protection device being introduced into the aorta.

Referring to FIG. 2, in one embodiment, embolic protection device 150 includes a first filter in the nature of proximal basket 200. Proximal basket 200 is a collapsible/expandable mesh basket with pores that are large enough to allow for the passage of blood, but small enough to trap emboli passing into proximal basket 200.

Embolic protection device 150, attached to the distal end of catheter 230 (shown in FIG. 4), is introduced into or near the ostium of a blood vessel, such as brachiocephalic artery 106 of aortic arch 110, via introducer sheath 270. Introducer sheath 270 may be initially introduced into the femoral artery, subclavian artery, or other vessel as is known in the art. During introduction, proximal basket 200 is in a collapsed state within introducer sheath 270. Once introducer sheath 270 is placed near the ostium of brachiocephalic artery 106, catheter 230 is pushed distally until proximal basket 200 exits the confines of introducer sheath 270. For embodiments in which proximal basket 200 is a collapsible/expandable mesh basket, proximal basket 200 will automatically open to its expanded configuration as seen in FIG. 2. The expansion is such that substantially all the blood flowing through brachiocephalic artery 106 passes through proximal basket 200.

Figure 3:
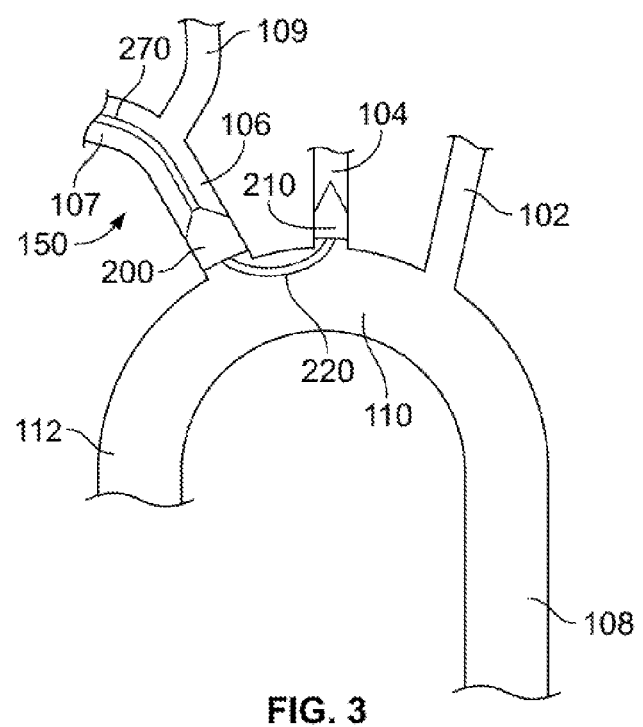
FIG. 3 illustrates a schematic view of a distal basket of the embolic protection device of FIG. 2 being deployed into the left common carotid artery.

Now referring to FIG. 3, once proximal basket 200 is expanded in brachiocephalic artery 106, a second filter, in the nature of distal basket 210, is then deployed. Distal basket 210 is connected to steerable guidewire 220 which extends through proximal basket 200 and into catheter 230 (shown in FIG. 4). Distal basket 210 may also take the form of a collapsible/expandable mesh basket with pores that are large enough to allow for the passage of blood, but small enough to trap emboli passing into distal basket 210. Prior to deployment, for example during introduction into the body, distal basket 210 may be collapsed within proximal basket 200, which itself is in a collapsed configuration. During deployment, distal basket 210 may automatically open to its expanded configuration once pushed distally out of proximal basket 200 via steerable guidewire 220. In its expanded configuration, distal basket 210 can be directed to or near the ostium of a nearby vessel, such as left common carotid artery 104, using steerable guidewire 220.

With both baskets 200, 210 expanded in the desired blood vessel, a cardiac or vascular intervention or other procedure can be performed. Such a cardiac or vascular intervention or other procedure may dislodge or otherwise result in emboli moving through the blood. If an embolus travels into the path of the expanded proximal basket 200 or distal basket 210, the embolus will become trapped in the mesh of the respective basket. Baskets 200, 210 remain in the expanded configuration for the duration of the cardiac or vascular interventional procedure. Once the interventional procedure is complete, distal basket 210 can be cinched closed to trap any emboli therein. After cinching, distal basket 210 is pulled into proximal basket 200, and both baskets 200, 210 and catheter 230 are removed from the patient along with any emboli trapped during the procedure. As catheter 230 and baskets 200, 210 pass back into introducer sheath 270, baskets 200, 210 are forced into a collapsed configuration inside introducer sheath 270. The cinching and removal steps are described more fully below with reference to FIGS. 6-7.

Figure 4:
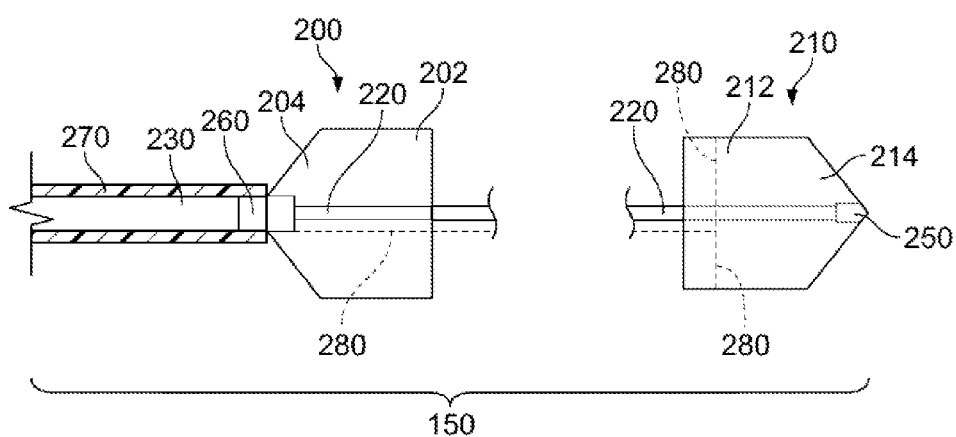
FIG. 4 illustrates a sectional side view of the embolic protection device of FIGS. 2-3 including the distal basket and the proximal basket according to an embodiment of the present disclosure.

Referring now to FIG. 4, embolic protection device 150 shown in FIGS. 2-3 is illustrated in further detail. Baskets 200, 210 each have a cylindrically shaped open portion 202, 212, with a conically shaped closed end portion 204, 214 respectively. Baskets 200, 210 are each formed of a braided mesh structure supported by struts 240 (struts 240 illustrated in FIG. 5).

For example, the mesh of baskets 200, 210 can be a braided superelastic metal alloy such as nickel-titanium alloy of the type sold under the designation NITINOL. As one example, 32-strand NITINOL braid may be used. Alternately, or in addition, 72-strand or 144-strand NITINOL braid may be used. A braid of approximately 0.0010-0.0015 inch (0.025-038 mm) diameter can be used for the mesh of baskets 200, 210.

Still referring to FIG. 4, distal basket 210 is coupled to steerable guidewire 220, which extends through proximal basket 200 and further through catheter 230. As illustrated in FIG. 4, closed end portion 204 of proximal basket 200 faces the proximal end of embolic protection device 150. Cylindrically shaped open portion 202 of proximal basket 200 faces the distal end of embolic protection device 150. Distal basket 210 is generally in line with proximal basket 200 by virtue of steerable guidewire 220, but in the opposite orientation. As such, cylindrically shaped open portion 212 of distal basket 210 faces the proximal end of embolic protection device 150, and closed end portion 214 faces the distal end of embolic protection device 150.

The shape of proximal basket 200 and distal basket 210 is maintained by virtue of the shape-maintaining material forming the baskets 200, 210. For example, NITINOL can be heat set to a particular shape, such as the generally cylindrical and/or conical shapes described above with reference to baskets 200, 210. The process of heat setting is described in greater detail below with reference to FIGS. 8-14. Baskets 200, 210 are also elastic such that they each may be radially collapsed into a collapsed configuration. The collapsed configuration may be particularly useful for creating a low profile of baskets 200, 210, such that they may be delivered into the body in an introducer sheath 270 in the low profile collapsed condition. The shape memory of baskets 200, 210 helps ensure that, upon a reduction of compressive forces, baskets 200, 210 automatically radially expand from the low profile, collapsed condition into the expanded configuration. The shape taken in the expanded configuration is dictated by the shape in which the material was heat set.

The distal end of steerable guidewire 220 is connected to end screw 250 of distal basket 210. End screw 250 is internally threaded to threadingly engage with external threads on the distal end of steerable guidewire 220. Other mating configurations are also possible, for example external threading on end screw 250 and internal threading on steerable guidewire 220. Steerable guidewire 220 extends distally from end screw 250 through an approximate midline of proximal basket 200. Steerable guidewire 220, having an outer diameter smaller than the inner diameter of catheter 230, extends further distally through an approximate midline of catheter 230. The proximal end of the steerable guidewire 220 can extend to a proximal end of the system (not shown) where a user is able to steer guidewire 220, and in turn, steer distal basket 210. Steerable guidewire 220 may, for example, include a pullable guidewire having at least one relatively stiff portion and one relatively flexible portion for positioning distal basket 210. Steerable guidewire 220 may include a pushable guidewire to which tension may be applied to steer distal basket 210 into the desired location. Mechanisms for steerable guidewires are known in the art and not described further herein.

The proximal end of proximal basket 200 is coupled to hypotube 260, which, in turn, is coupled to the distal end of catheter 230. Hypotube 260 may be formed as an integral part of catheter 230 or may be separately attached, such as with adhesives or through welding. The outer diameter of catheter 230 is small enough to pass through the inner diameter of introducer sheath 270. For example, the catheter 230 may be between about 3-15 French, 4-12 French, 5-8 French, or approximately 6-7 French.

Still referring to FIG. 4, elongated cinch wire 280 (shown as a broken line), which may for example be a suture or other suitable cable-type material, extends generally around the circumference of cylindrical portion 212 of distal basket 210 and back through proximal basket 200 and catheter 230. Cinch wire 280 may, for example, weave in and out of the mesh structure of distal basket 210 in a purse string configuration. Cinch wire 280 may additionally or alternately attach circumferentially to two or more struts 240 (described in more detail below with reference to FIG. 5) in distal basket 210. Cinch wire 280 extends through the catheter 230 to a proximal end (not shown) where the user is able to control cinch wire 280, for example, with a pulling motion. Pulling cinch wire 280 proximally causes distal basket 210 to constrict at the point of attachment, much like pulling a purse string. This functions to further secure emboli trapped in distal basket 210, described in more detail below with reference to FIGS. 6-7.

Figure 5:
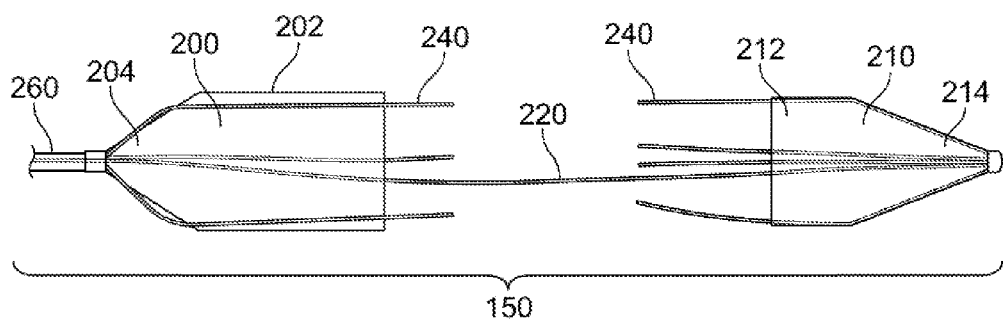
FIG. 5 illustrates a side view of the embolic protection device of FIG. 4.

Now referring to FIG. 5, the mesh of baskets 200, 210 can be structurally reinforced with struts 240, such as solid, elongated pieces of superelastic metal alloy, such as NITINOL. In one example, each strut 240 is between about 0.005-0.015 inches (0.127-0.381 mm) or approximately 0.010 inches (0.254 mm) in diameter. Each strut 240 is about ten times as thick as the mesh braid and aids baskets 200, 210 in maintaining the generally cylindrical shape of open portions 202, 212. By helping to maintain the generally cylindrical shape of open portions 202, 212, struts 240 also help ensure that baskets 200, 210 maintain contact with the walls of vessels in which they are deployed. Referring back to FIG. 3, for example, struts 240 help proximal basket 200 maintain contact with the walls of brachiocephalic artery 106. Similarly, struts 240 help distal basket 210 maintain contact with the walls of left common carotid artery 104. This contact of baskets 200, 210 to the walls of the blood vessels increases the likelihood of trapping emboli that pass into the blood vessels.

Now referring back to FIG. 5, each basket 200, 210 can have one or more struts 240 and the exact number of struts in each basket 200, 210 is largely a matter of design choice. Generally, more struts 240 in a basket results in an improved ability of the mesh to maintain its cylindrical shape when in the expanded condition. However, more struts 240 in a basket results in an increased profile of the basket when the basket is in the collapsed configuration. Therefore the specific number and design of struts 240 in proximal basket 200 and distal basket 210 depends on the materials used, the particular application of the device, and the desired performance of the device.

Generally, struts 240 in proximal basket 200 are spaced equally around cylindrically shaped portion 202. For example, three struts would be placed 120° apart, four struts would be placed 90° apart, etc. Each strut 240 begins distal to the distal end of cylindrically shaped open portion 202 of proximal basket 200. Struts 240 extend proximally, generally parallel to, and along the surface of, cylindrically shaped open portion 202. Struts 240 follow the surface of proximal basket 200 and curve toward conical closed end portion 204. All struts 240 in proximal basket 200 meet at conical closed end portion 204. The structure of struts 240 in distal basket 210 is similar, with the directionality being reversed. In other words, struts 240 of distal basket 210 extend past the mesh of distal basket 210 in the proximal direction, and each meet at the proximal conical closed end portion 214.

In the embodiment illustrated in FIG. 5, proximal basket 200 includes three struts 240 while distal basket 210 includes four struts. As will become clear below, the ability of distal basket 210 to achieve a small profile is one design factor. As such, in an embodiment, distal basket 210 has fewer struts 240 than proximal basket 200, such as three struts in distal basket 210 and four struts in proximal basket 200. The process for manufacturing baskets 200, 210, including struts 240, is described in more detail below with reference to FIGS. 8-10.

Figure 6:
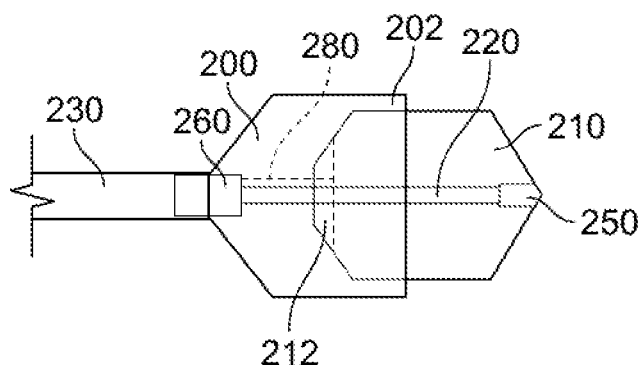
FIG. 6 illustrates a sectional side view of the embolic protection device of FIG. 4 with the distal basket cinched and being retracted into the proximal basket.

Now referring to FIG. 6, distal basket 210 is illustrated cinched closed and being retracted into proximal basket 200. After insertion of embolic protection device 150 and completion of a surgical intervention, embolic protection device 150 is extracted from the patient. Prior to extraction, distal basket 210 is retracted proximally into proximal basket 200. Prior to the retraction step, distal basket 210 is cinched closed to reduce the likelihood of emboli escaping distal basket 210 and re-entering the blood stream. As described above with reference to FIG. 4, pulling cinch wire 280 causes distal basket 210 to constrict like pulling a purse string. In an embodiment, the pulling force required to cinch distal basket 210 closed is minimal and does not substantially cause movement of distal basket 210 proximally toward proximal basket 200.

The constricting action allows distal basket 210, with any trapped emboli therein, to be fully or nearly fully sealed before attempting to retract distal basket 210 into proximal basket 200. Any agitation of baskets 200, 210 may increase the likelihood of a trapped embolus escaping back into the blood stream. Such agitation may occur when retracting distal basket 210 into proximal basket 200. By fully, or nearly fully, sealing open portion 212 of distal basket 210 with cinch wire 280 prior to retraction, the likelihood of an embolus trapped within distal basket 210 inadvertently re-entering the blood stream during retraction is significantly reduced.

In other words, prior to cinching, distal basket 210 is in the expanded configuration, with open end 212 having a pre-cinched diameter. The cinching action collapses open end 212 of distal basket 210 to a smaller, post-cinched diameter. This is possible due to the expandable/collapsible nature of distal basket 210. Even when open portion 212 is collapsed due to the cinching action, the rest of distal basket 210 remains in a generally expanded configuration. The post-cinched diameter of open portion 212 is smaller than the diameter of open portion 202 of proximal basket 200 when proximal basket 200 is in the expanded configuration. These relative diameters help ensure that open portion 212 of distal basket 210 can be retracted into open portion 202 of proximal basket 200 after being cinched.

Figure 7:
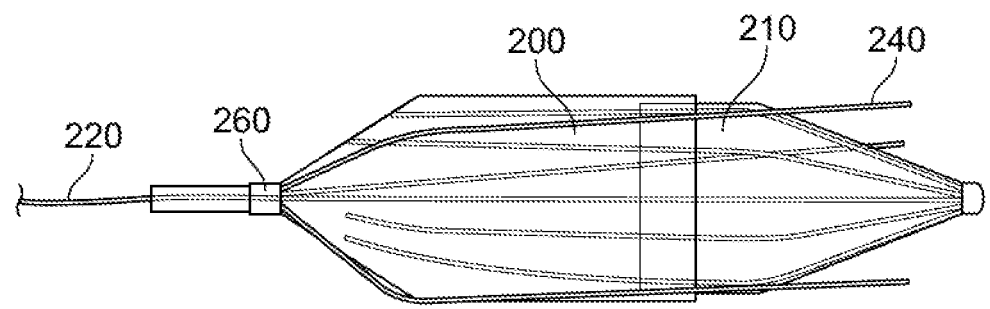
FIG. 7 illustrates a side view of the embolic protection device of FIG. 4 with the distal basket retracted into the proximal basket.

Now referring to FIG. 7, distal basket 210 is illustrated retracted into proximal basket 200. The user may accomplish this by pulling steerable guidewire 220 proximally until open end 212 of distal basket 210 is proximal of open end 202 of proximal basket 200. In this configuration, distal basket 210 and proximal basket 200 form a fully or nearly fully sealed filter unit. Distal basket 210 and proximal basket 200 can be considered a sealed filter unit in this configuration because distal basket 210 partially or fully occupies open cylindrical portion 202 of proximal basket 200. During extraction of embolic protection device 150, both distal basket 210 and proximal basket 200 are radially collapsed and removed through introducer sheath 270, as described above with reference to FIG. 4. These movements may agitate emboli trapped within proximal basket 200 or distal basket 210. However, because distal basket 210 is located partially within proximal basket 200 during the collapsing action as a sealed filter unit, agitated emboli are unlikely to escape back into the blood stream. As proximal basket 200 and distal basket 210 proximally pass through introducer sheath 270, baskets 200, 210 radially collapse into introducer sheath 270. Once in the collapsed configuration, both baskets 200, 210 can be extracted from the patient, with any emboli trapped during the interventional procedure securely remaining within the confines of the collapsed baskets 200, 210 throughout extraction.

Turning now generally to FIGS. 8-14, devices useful for the manufacturing of proximal and distal baskets 200, 210 are shown. To produce proximal and/or distal baskets 200, 210, tubular braided mesh 242 (illustrated in FIG. 9) is fitted over inner mold 300, as seen in FIG. 8. Inner mold 300 provides a structure upon which proximal basket 200 or distal basket 210 may be formed. Inner mold 300 can be formed from a range of materials that withstand heating, are commonly available, are durable and have good heat transfer properties. For example, brass or similar materials can be used for the inner mold 300. In the illustrated embodiment, inner mold 300 resembles the shape of proximal and distal baskets 200, 210, having generally cylindrical portion 305 and conical portion 310. The interior of cylindrical portion 305 can include hollow portion 315. Hollow portion 315 may reduce the mass of inner mold 300 and reduce the time necessary for any heating or cooling of inner mold 300.

The dimensions of inner mold 300 can be varied for baskets of different sizes. For example, the following dimensions of inner mold 300 may be useful for forming proximal basket 200. Height $H_1$ of cylinder portion 305 is between about 1-2 inches (25.4-50.8 mm) or approximately 1.5 inches (38.1 mm). Height $H_2$ of conical portion 310 is between about 0.5-1.1 inches (12.7-27.94 mm) or approximately 0.8 inches (20.32 mm). Diameter $D_1$ of hollow portion 315 is between about 0.25-0.75 inches (6.35-19.05 mm) or approximately 0.5 inches (12.7 mm). Diameter $D_2$ of cylindrical portion 305 is between about 0.5-1 inches (12.7-25.4 mm) or approximately 0.748 inches (19 mm). Angle α of conical portion 310 is between about 15°-25°, or approximately 20°.

Inner mold 300 with a similar shape but different dimensions can be used for distal basket 210. For example, the following dimensions of inner mold 300 may be useful for forming distal basket 210. Height $H_1$ of cylinder portion 305 is between about 1-2 inches (25.4-50.8 mm) or approximately 1.5 inches (38.1 mm). Height $H_2$ of conical portion 310 is between about 0.25-0.75 inches (6.35-19.05 mm) or approximately 0.5 inches (12.7 mm). Diameter $D_1$ of hollow portion 315 is between about 0.25-0.75 inches (6.35-19.05 mm) or approximately 0.5 inches (12.7 mm). Diameter $D_2$ of cylindrical portion 305 is between about 0.5-1 inches (12.7-25.4 mm) or approximately 0.787 inches (20 mm). Angle α of conical portion 310 is between about 25°-35°, or approximately 30°.

The provided dimensions are merely illustrative and are in no way meant to limit the scope of the disclosure. These dimensions can be varied for different preferences or applications. For example, in one embodiment, inner mold 300 used to form proximal basket 200 has a larger diameter $D_2$ of cylindrical portion 305 than inner mold 300 used to form distal basket 210. In this embodiment, the larger diameter $D_2$ of proximal basket 200 inner mold 300 results in a larger diameter of proximal basket 200. This configuration may make it easier to retract distal basket 210 into proximal basket 200, described above in relation to FIG. 7.

Once tubular braided mesh 242 is on inner mold 300, struts 240 are inserted between the mesh and inner mold 300 in the desired configuration. Struts 240 may be equally spaced. For example, in a basket with four struts 240, the struts may be placed every 90°, whereas in a basket with three struts, the struts may be placed every 120°. The number and exact spacing of struts 240, however, is largely a matter of design choice as discussed in detail above.

Referring now to FIG. 9, placement of two struts 240a, 240b within braided mesh 242 is illustrated. Inner mold 300 is omitted from FIG. 9 for clarity of illustration. Each strut 240a, 240b is initially placed between braided mesh 242 and cylindrical portion 305 of inner mold 300. Struts 240a, 240b are advanced toward conical portion 310 of inner mold, and are passed through the mesh near the angled transition of inner mold 300 from cylindrical portion 305 to conical portion 310. Struts 240a, 240b are then woven back inside the mesh and guided toward the tip of conical portion 310.

To aid in the introduction and weaving of struts 240, the outer surface of cylindrical portion 305 of inner mold 300 can include a plurality of notches or grooves 320 running the length of cylindrical portion 305. As shown in FIG. 10, grooves 320 aid in inserting struts 240 between braided mesh 242 and inner mold 300, especially if braided mesh 242 is tightly fitted over inner mold 300.

For proximal basket 200, after guiding struts 240 toward the tip of the conical portion 310, struts 240 are situated on or near the outer surface of a cylindrical structure, such as hypotube 260 (illustrated in FIGS. 5-6). Hypotube 260 can be between about 0.125-0.375 inches long (3.175-9.525 mm), or approximately 0.25 inches long (6.35 mm). Hypotube 260 is between about 10-15 gauge, or approximately 13 gauge. Struts 240 are then cinched to hypotube 260 by a marker band (not illustrated). Marker bands are known in the art and can be formed of, for example, a radiopaque material such as platinum iridium that allows for visualization inside the body. Struts 240, the marker band and hypotube 260 are joined together, such as by adhesives, soldering, brazing, or laser welding to remove any excess material.

For distal basket 210, after guiding struts 240 toward the tip of conical portion 310 of inner mold 300, struts 240 are joined with the braid atop of end screw 250 (shown in FIG. 4) and cinched using a marker band. Struts 240, the marker band and end screw 250 are joined together, such as by adhesives, soldering, brazing, or laser welding to remove any excess material.

Figure 11:
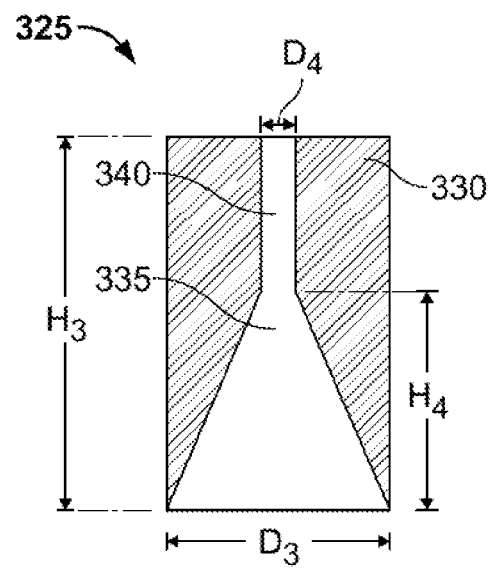
FIG. 11 illustrates a vertical sectional view of an outer mold used to produce a filter for an embolic protection device according to an embodiment of the present disclosure.

Now referring to FIG. 11, outer mold 325 is illustrated. After welding proximal basket 200, outer mold 325 is placed over the conical portion 310 of the inner mold, sandwiching braided mesh 242 therebetween. Outer mold 325 includes cylindrical portion 330 and hollow conical portion 335 within cylindrical portion 330. Hollow conical portion 335 is generally dimensioned to correspond to conical portion 310 of inner mold 300. Outer mold 325 can also include hollow conduit 340 connecting the tip of hollow conical portion 335 to the outside of outer mold 325. Hollow conduit 340 is dimensioned to accept hypotube 260 and other elements extending from the tip of conical portion 204 of proximal basket 200.

Outer mold 325, which can be used while forming proximal basket 200, can be a variety of sizes depending on the desired size of proximal basket 200. In one embodiment, height $H_3$ of outer mold 325 is between about 1-2 inches (25.4-50.8 mm) or approximately 1.5 inches (38.1 mm). Height $H_4$ of hollow conical portion 335 is between about 0.5-1.1 inches (12.7-27.94 mm) or approximately 0.8 inches (20.32 mm). Diameter $D_3$ of outer mold 325 is between about 0.5-1.0 inches (12.7-25.4 mm) or approximately 0.748 inches (19 mm). Diameter $D_4$ of hollow conduit 340 is between about 0.125 inches and 0.25 inches (3.175-6.35 mm) or approximately 0.1875 inches (4.76 mm). As with inner mold 300, outer mold 325 may be formed from a range of materials that withstand heating, are commonly available, are durable and have good heat transfer properties. For example, brass or similar materials can be used for outer mold 325.

Figure 12:
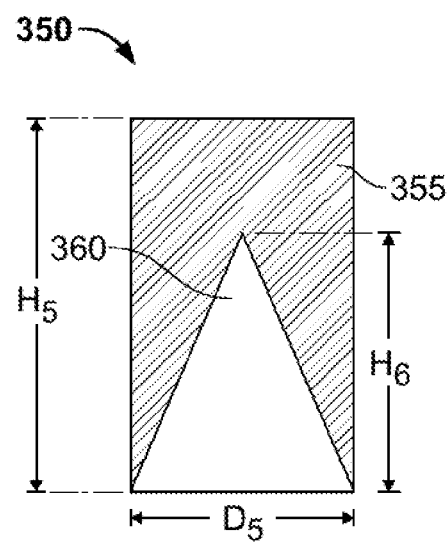
FIG. 12 illustrates a vertical sectional view of an alternate embodiment of an outer mold used to produce a filter for an embolic protection device according to an embodiment of the present disclosure.

Now referring to FIG. 12, outer mold 350 is illustrated. After welding distal basket 210, outer mold 350 is placed over conical portion 310 of inner mold 300, sandwiching braided mesh 242 therebetween. Outer mold 350 includes cylindrical portion 355 and hollow conical portion 360 within cylindrical portion 355. Hollow conical portion 360 is generally dimensioned to correspond to conical portion 310 of inner mold 300.

Outer mold 350, which can be used while forming distal basket 210, can be a variety of sizes depending on the desired size of distal basket 210. In one embodiment, height $H_5$ of outer mold 350 is between about 1-2 inches (25.4-50.8 mm) or approximately 1.5 inches (38.1 mm). Height $H_6$ of the hollow conical portion 360 is between about 0.25-0.75 inches (6.35-19.05 mm) or approximately 0.5 inches (12.7 mm). Diameter $D_5$ of outer mold 350 is between about 0.5-1 inches (12.7-25.4 mm) or approximately 0.787 inches (20 mm). As with inner mold 300, outer mold 350 may be formed from a range of materials that withstand heating, are commonly available, are durable and have good heat transfer properties. For example, brass or similar materials can be used for outer mold 350.

Figure 13:
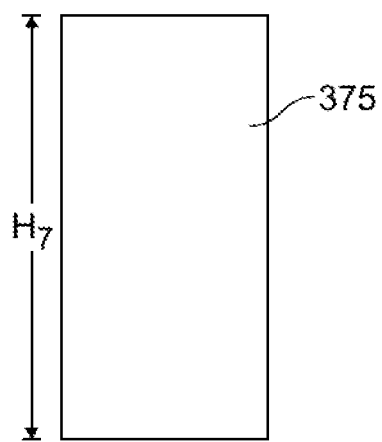
FIG. 13 illustrates a side view of a clam shell used to produce a filter for an embolic protection device according to an embodiment of the present disclosure.
Figure 14:
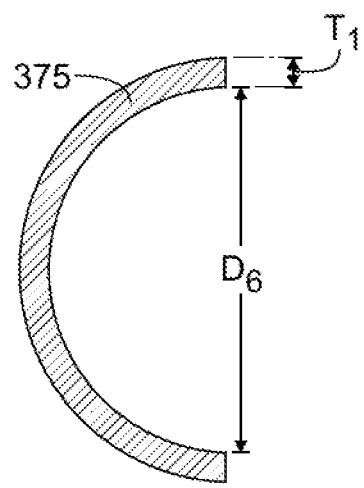
FIG. 14 illustrates a top view of the clam shell of FIG. 13.

Referring to FIGS. 13-14, clam shell 375 is illustrated in side and top views, respectively. A pair of clam shells 375 (only one clam shell illustrated in FIGS. 13-14) may be used in conjunction with inner mold 300, as well as either outer mold 325 or outer mold 350, to sandwich braided mesh 242 into the desired configuration. Each clam shell 375 approximates a hollow half-cylinder, generally corresponding to the shape of cylindrical portion 305 of inner mold 300. Two clam shells 375 are each fitted over opposing sides of cylindrical portion 305 of inner mold 300. Since each clam shell 375 approximates a hollow half cylinder, two clam shells 375 form an outer hollow cylinder that completely surrounds and sandwiches cylindrical portion 305 of inner mold 300.

An embodiment of clam shell 375 that can be used with inner mold 300 may have height $H_7$ of between about 1-2 inches (25.4-50.8 mm) or approximately 1.5 inches, (38.1 mm). Clam shell 375 may have thickness $T_1$ of between about 0.075-0.175 inches (1.9-4.45 mm) or approximately 0.125 inches (3.175 mm). If clam shell 375 is used to form proximal basket 200, it may have diameter $D_6$ of between about 0.760-1.01 inches (19.3-25.65 mm). If clam shell 375 is used to form distal basket 210, it may have diameter $D_6$ of between about 0.799-1.049 inches (20.29-26.64 mm). As with inner mold 300, clam shells 375 may be formed from a range of materials that withstand heating, are commonly available, are durable and have good heat transfer properties. For example, brass or similar materials can be used for clam shells 375.

The clam shells 375 may be fitted onto cylindrical portion 305 of inner mold 300 before, after, or at the same time that either outer mold 235 (if forming proximal basket 200) or outer mold 350 (if forming distal basket 210) is fitted onto conical portion 310 of inner mold 300. Outer mold 325 or outer mold 350 may simply rest on top portions of clam shells 375, and need not attach to clam shells 375. As described above with reference to FIGS. 8 and 11-14, braided mesh 242 is fitted over inner mold 300 and surrounded on top by outer mold 325 (or outer mold 350) and surrounded on the sides by two clam shells 375. Once braided mesh 242 is sandwiched on all sides, it takes the shape of the molds applied. In this embodiment, the shape is a cylinder which is open on one side and which is conical on the other side.

When braided mesh 242 is a material that has shape memory, such as NITINOL, the sandwiched braid may be heated to set the desired shape. The assembly including inner mold 300, outer mold 325 (or outer mold 350), clam shells 375 and sandwiched mesh with struts 240 is heated. A thermocouple lead may be used near the mesh to determine temperature of the mesh. The mesh is heated to between about 475°-575° C., or approximately 530° C., to set the shape of the mesh. For different mesh materials, and even for different compositions of NITINOL, different temperatures may be required for heat setting. Once set, the assembly is cooled, for example in an ambient water bath. Once cooled, clam shells 375 and outer mold 325 (or outer mold 350) may be removed. The mesh may be taken off inner mold 300, with the end product being proximal basket 200 (if outer mold 325 was used) or distal basket 210 (if outer mold 350 was used). Any excess mesh or struts 240 may be trimmed.

All provided dimensions, temperatures, angles, and materials are merely illustrative and are in no way meant to limit the scope of the disclosure. For example larger or smaller inner molds 300, outer molds 325, 350 and clam shells 375 may be used for larger or smaller baskets to be used in larger or smaller vessels in the body.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure.

The invention claimed is:

1. An embolic protection device, comprising:
a first filter having an open end having a cylindrical shape and a second end opposite the open end having a conical shape, the second end being connected to a tube having a conduit;
a first plurality of struts positioned at least partially inside the first filter for maintaining the cylindrical shape of the open end of the first filter, each of the struts extending from a first strut end near the second end of the first filter to a free strut end positioned beyond the open end of the first filter;
a second filter having an open end having a cylindrical shape and a closed end having a conical shape, the second filter having a mesh structure and being connected to a first wire, the first wire extending into the conduit of the tube;
a second plurality of struts positioned at least partially inside the second filter for maintaining the cylindrical shape of the open end of the second filter, the second plurality of struts extending from a first strut end near the closed end of the second filter to a free strut end positioned beyond the open end of the second filter; and
a second wire having a first portion and a second portion, the first portion of the second wire being circumferentially interwoven through the mesh structure of the open end of the second filter, the second portion of the second wire extending into the conduit of the tube,
wherein the open end of the first filter confronts the open end of the second filter and the second end of the first filter is spaced farther away from the closed end of the second filter than the open end of the second filter in an operative condition, and the second filter is at least partially receivable within the first filter in an assembled condition so that the free ends of the second plurality of struts are positioned within the first filter,
wherein the second filter has an uncinched expanded condition and a cinched expanded condition, the shape of the conical end of the second filter being generally the same in the uncinched expanded condition and the cinched expanded condition of the second filter, and a diameter of the open end of the second filter being smaller in the cinched expanded condition than in the uncinched expanded condition so that, in the cinched expanded condition, the free strut ends of the second plurality of struts are positioned closer to one another than in the uncinched expanded condition of the second filter.

2. The device of claim 1, wherein the first filter has a mesh structure.

3. The device of claim 2, wherein the first filter and the second filter are each expandable and collapsible.

4. The device of claim 1, wherein the first wire is a steerable guide wire.

5. The device of claim 2, wherein the first plurality of struts is interwoven through the mesh structure of the first filter and the second plurality of struts is interwoven through the mesh structure of the second filter.

6. The device of claim 1, further comprising:
a first radiopaque marker attached to the closed end of the first filter; and
a second radiopaque marker attached to the closed end of the second filter.

7. The device of claim 1, wherein the first portion of the second wire encircles the second plurality of struts in the second filter.

8. The device of claim 1, wherein pulling the second portion of the second wire transitions the second filter from the uncinched expanded condition to the cinched expanded condition.

9. The device of claim 8, wherein pulling the second portion of the second wire does not cause substantial movement of the first filter with respect to the second filter.

10. The device of claim 1, wherein the first wire extends through the open end of the first filter.

11. The device of claim 1, wherein the second portion of the second wire extends through the open end of the first filter.

12. The device of claim 11, wherein the second portion of the second wire extends through both the open end of the first filter and the second end of the first filter.

13. The device of claim 11, wherein the second wire is a suture.

14. The device of claim 11, wherein the second wire is a cable.

15. The device of claim 11, wherein the second wire is interwoven through the mesh structure of the open end of the second filter in a purse string configuration.

16. The device of claim 1, wherein the free ends of the first plurality of struts are positioned outside the second filter in the assembled condition.

17. The device of claim 1, wherein the cylindrical shape of the first filter extends a first distance and the conical shape of the first filter extends a second distance, the first distance being greater than the second distance.

18. The device of claim 1, wherein each of the first plurality of struts has a first section extending from the first strut end to a strut transition where the conical shape of the first filter transitions to the cylindrical shape of the first filter, and a second section extending from the strut transition to the free strut end, the second section being longer than the first section.

19. The device of claim 1, wherein each of the second plurality of struts has a first section adjacent the conical shape of the second filter, and a second section adjacent the free strut end, the first sections having substantially the same position relative to one another in the cinched expanded condition and in the uncinched expanded condition of the second filter.

* * * * *